(12) United States Patent
Ghezzi et al.

(10) Patent No.: US 7,964,137 B2
(45) Date of Patent: Jun. 21, 2011

(54) SHORT-CYCLE STERILISATION SYSTEM FOR AUTOCLAVE AND OPERATION METHOD THEREOF

(75) Inventors: Fabio Ghezzi, Cusano Milanino (IT); Daniele Ongaro, Villa Di Serio (IT); Marco Parolini, Giandino (IT); Christian Stempf, Gorle (IT); Walter Crotti, Alme' (IT)

(73) Assignee: W & H Sterilization S.r.l., Brusaporto (Bergamo) (IT)

( * ) Notice: Subject to any disclaimer, the term of this patent is extended or adjusted under 35 U.S.C. 154(b) by 480 days.

(21) Appl. No.: 12/280,687

(22) PCT Filed: Feb. 27, 2007

(86) PCT No.: PCT/IB2007/050630
§ 371 (c)(1),
(2), (4) Date: Aug. 26, 2008

(87) PCT Pub. No.: WO2007/099498
PCT Pub. Date: Sep. 7, 2007

(65) Prior Publication Data
US 2009/0169423 A1       Jul. 2, 2009

(30) Foreign Application Priority Data

Feb. 28, 2006   (IT) .............................. MI2006A0363
Oct. 4, 2006    (IT) ............................. MI20060340 U

(51) Int. Cl.
| A61L 2/08  | (2006.01) |
| A61L 9/00  | (2006.01) |
| A61L 2/00  | (2006.01) |
| G01N 27/00 | (2006.01) |
| G05D 23/00 | (2006.01) |
| F28F 27/00 | (2006.01) |

(52) U.S. Cl. .................... 422/26; 422/1; 422/3; 422/27; 422/28; 422/29; 422/32; 422/62; 422/83; 422/82.12; 422/82.13; 422/98; 422/108; 422/109; 422/119; 422/295; 422/298; 422/305; 165/2; 165/200; 165/901

(58) Field of Classification Search .................. 422/1, 3, 422/26–29, 32, 62, 83, 82.12, 82.13, 98, 422/108, 109, 119, 295, 298, 305; 165/2, 165/200, 901
See application file for complete search history.

(56) References Cited

U.S. PATENT DOCUMENTS
4,497,773 A   2/1985   Kuelzow et al.
5,277,875 A   1/1994   Albright et al.

FOREIGN PATENT DOCUMENTS
| AU | 526 378 B2      |   | 1/1983 |
| DE | 35 05 340 A1    |   | 8/1986 |
| US | AU-B-44120/79   | * | 1/1983 |
| WO | 2005/004931 A1  |   | 1/2005 |

* cited by examiner

OTHER PUBLICATIONS
European machine translation PDF document of AU-B-44120/79.*

*Primary Examiner* — Jill Warden
*Assistant Examiner* — Monzer R Chorbaji
(74) *Attorney, Agent, or Firm* — Young & Thompson

(57) ABSTRACT

A control system of a surgery autoclave is described, which is capable of establishing a sterilization cycle which includes at least a first evacuation step of a sterilization chamber and of heating of a load and a final drying step. The autoclave includes a device capable of detecting a parameter proportional to the energy used up in a step of the cycle preceding the drying step and the control system establishes at least a reduction of the drying step upon determining that, the parameter of used up energy lies below a preset threshold.

17 Claims, 4 Drawing Sheets ic tools and products to be employed in
SHORT-CYCLE STERILISATION SYSTEM FOR AUTOCLAVE AND OPERATION METHOD THEREOF The present invention concerns a short-cycle sterilisation system for an autoclave and an operation method thereof. In particular it concerns a short-cycle system wherein it is nevertheless possible to comply with sterilisation rules and standards.

As known, surgery autoclaves are apparatuses for the sterilisation of medical tools and products to be employed in doctor's surgeries, typically in dental surgeries.

The sterilisation cycle performed by autoclaves can vary in its nature, but is generally suited to meet specific rules incorporated at international level. For example, an incorporated standard is EN13060, wherein a set of parameters of time, pressure, temperature and level of dryness are provided, which the sterilisation cycle must meet: a typical cycle provided in such rule is for example type "B".

Figure 1:
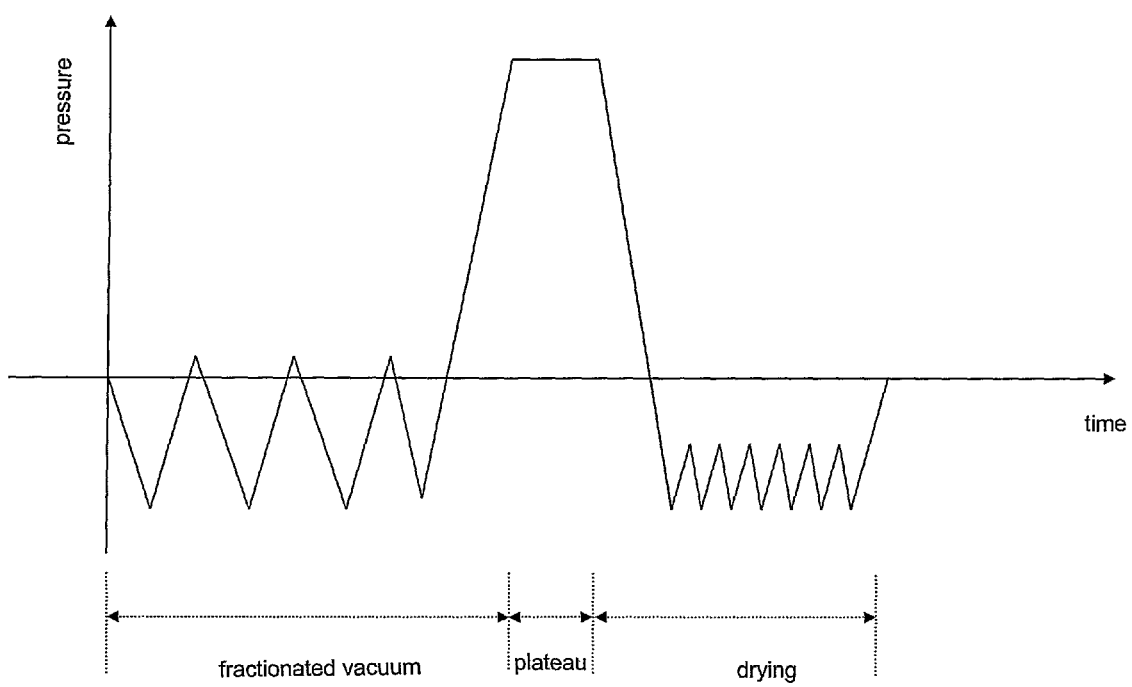

A type-B sterilisation cycle generally provides three main steps which come one after another: a first warming-up and fractionated-vacuum step, a second exposure step, and a third drying step. FIG. 1 shows an examplary curve of the pressure as a function of the time required for such a sterilisation cycle.

In the first step of fractionated vacuum, a series of subsequent steps of vacuum and steam injection is performed. The fractionated-vacuum cycles are performed reaching preset levels of vacuum and pressure for the purpose of removing residues of air (insulating) around and within the load cavities or porosities: therefore the duration of this step is strictly connected to load nature and size and, for example, in the autoclave LISA® manufactured by W&H Sterilization having a 17-lt chamber, a nominal power of 2100 W and a 134-Standard-type sterilisation cycle can last from a minimum of 10' to a maximum of 25' depending on load size.

Similar requirements, although different in parameter values, exist with other sterilisation cycle types, for example the 134-Prion type.

In order to comply with standards, it is hence not possible to artificially shorten this step—the power employed and volume of the autoclave being the same. The autoclave control system, in a manner known per se (for example by detecting pressure and time elapsed), is capable of automatically determining when sufficient evacuation conditions have been reached, and when it is possible to move on to the second step. Duration is hence not determined by the autoclave control system, but by the actual reaching of the parameters.

In the second exposure step—wherein the actual sterilisation occurs—the inside of the autoclave chamber, and consequently the load, is brought to a steam overpressure (typically to 2.16 relative bar and 135.5° C.) for a duration of at least 3'. The duration of this step is fixed and established by the standard of reference.

Finally, a drying step is performed, during which the chamber is progressively evacuated, for the purpose of removing any trace of dampness from the load, which can hence be subsequently stored into suitable sterile packages.

This last step is particularly critical for achieving a perfect drying of the load which would otherwise not be suitable for prolonged storage. Since under the circumstances it is not possible to determine in real time the degree of load dryness, standards provide profile validation criteria, which establish whether the set time is sufficient to achieve correct drying in the worst operation scenario, for example in the presence of the maximum expected load; for example, in the above-said autoclave LISA®, the drying time for a standard sterilisation cycle is set at 15'.

However, as can be understood, the duration of the drying step does not allow an optimisation of the process times should the worst case scenario not be applicable, for example when the load is smaller than the maximum expected load.

In substance, a full sterilisation cycle—for example a standard type-B cycle, performed with the autoclave LISA®—necessarily has an overall duration (resulting from the sum of the 3 steps) of about 30-45 minutes, although with a reduced load it could be completed also in a shorter time despite achieving full drying in compliance with the validation criteria provided by the standards of reference.

Although it can be provided that the operator acts to interrupt in advance the sterilisation cycle when a reduced load is to be treated—typically interrupting in advance the drying step—this would not at all be safe, because it would leave too much discretionary power to the user, with the risk of the cycle actually remaining incomplete and not complying with the standard of reference.

A first object of the present invention is hence that of offering a system which allows the execution wherever applicable, for example when the load is smaller than the maximum expected load, of a shortened sterilisation cycle, with the certainty of complying with regulation requirements—typically those of a so-called B-type cycle.

A further object is that of widening and optimising this concept also on cycles differing from the classic standard B-type cycle and in the presence of differentiated loads, preferably with a drying time optimised according to the load size to be treated.

Such objects are achieved by means of a system and a method as described in their essential features in the accompanying claims.

Figure 2:
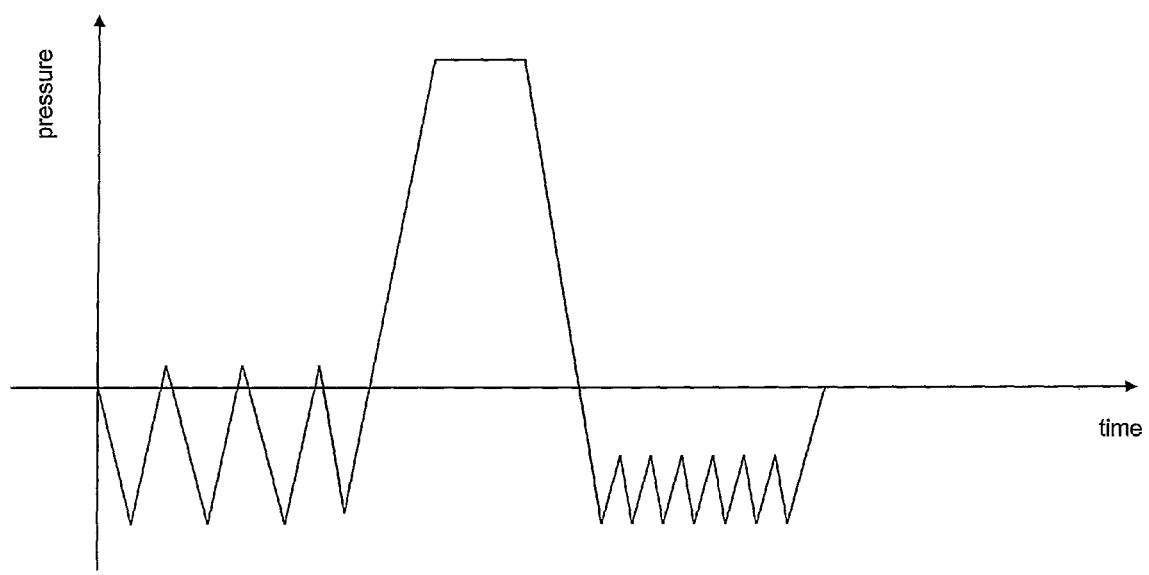
Figure 3:
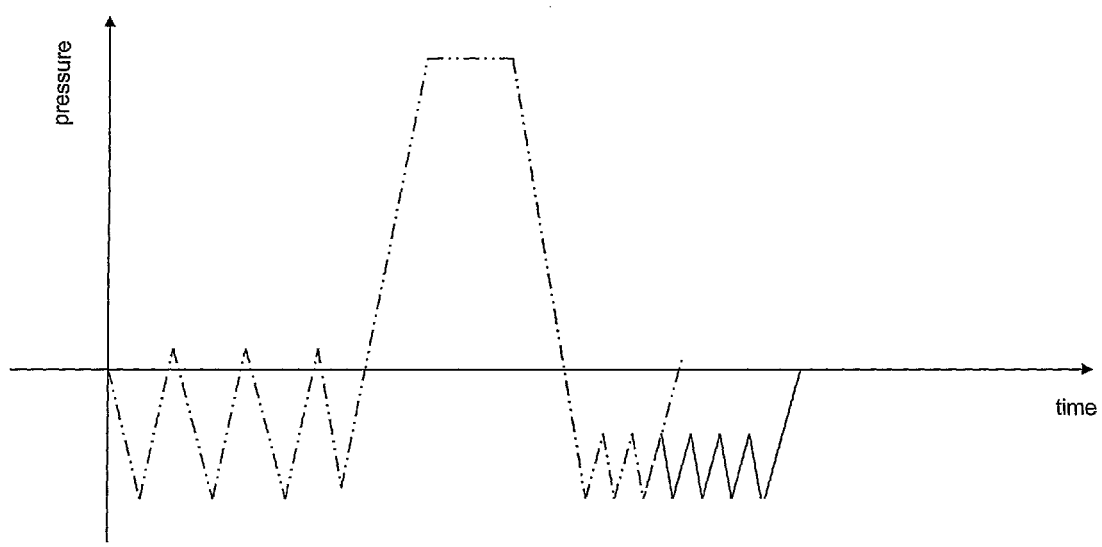
Figure 4:
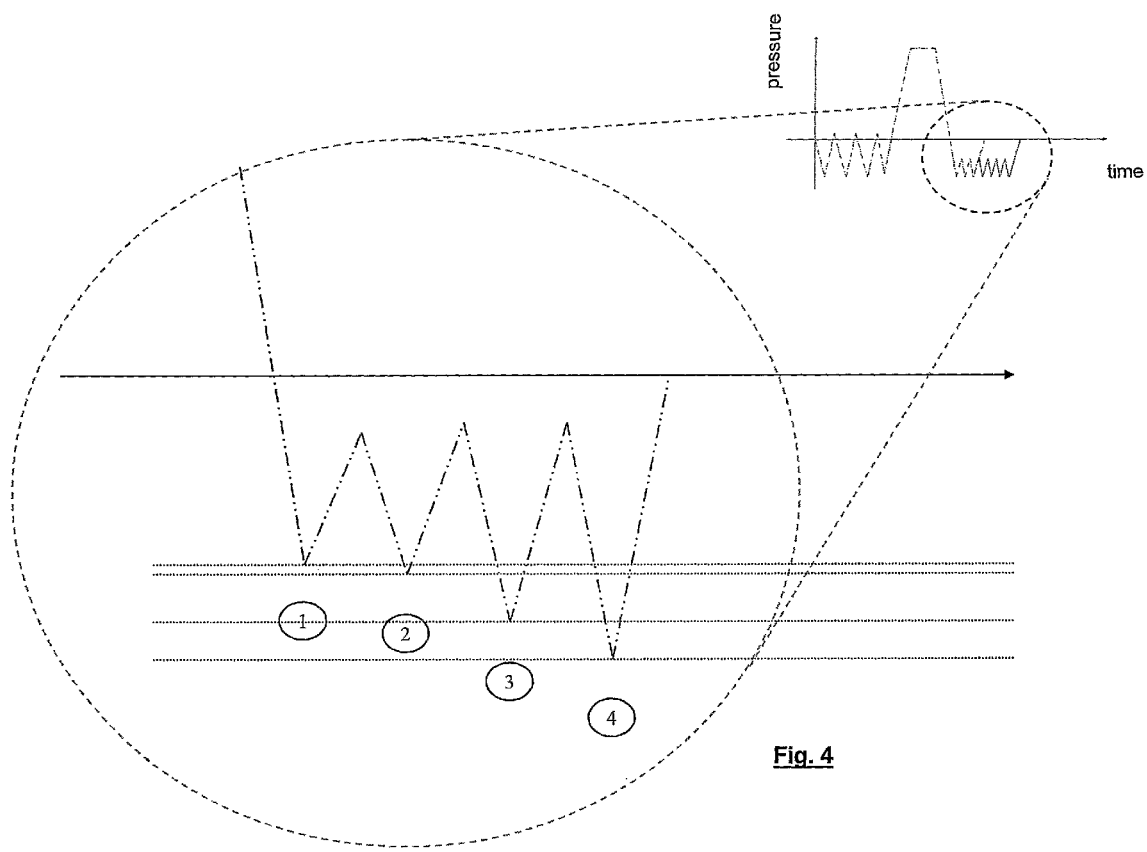

Further features and advantages of the system and of the method according to the invention will in any case be more evident from the following detailed description of a preferred embodiment of the same, given by way of example and illustrated in the accompanying drawings, wherein:

FIG. 1, as already mentioned, shows an example diagram of a standard sterilisation cycle with full load; and FIG. 2 shows an examplary diagram of a standard sterilisation cycle with a reduced load;

FIG. 3 shows a comparison between the diagram of FIG. 2 and a shortened sterilisation cycle according to the invention; and FIG. 4 shows a magnified portion of the diagram of FIG. 3.

The Applicant has conceived the inventive solution from the observation that, within a full sterilisation cycle, the drying step is the one which can determine—upon variation of the load to be sterilised—a power and a throughout difference of the system. As a matter of fact, this step, which according to the known art has a substantially fixed duration, uses an energy amount and lasts a certain time which, in the presence of reduced loads, are not essential for achieving the full drying required by standards.

The system of the invention hence provides to define a standard sterilisation profile, which may be used for the full load, and one or more "short" profiles which may be applied to reduced loads (nevertheless complying with regulations) wherein the duration of the drying step is substantially reduced.

In order to have the certainty that the load is actually reduced and can hence be declared compliant with the regulation also with a short profile, according to the invention the autoclave control system in substance monitors the amount of energy used during the first heating and fractionated-vacuum step, which in the last analysis is strictly linked to the quality and size of the load found in the chamber.

As a matter of fact, the greater the size of the load in the autoclave, the greater the amount of condensation occurring on the load, the greater the amount of water caused to evaporate, and hence the greater the duration of the first step and the energy used up.

According to a first embodiment, the amount of energy used up in the first step of the cycle is obtained as an indirect measurement, for example by measuring the time taken by the autoclave to reach the conditions to pass to the second step of the cycle. In a first approximation, this reading can be an efficient solution, also because it requires a minimum use of resources in terms of sensors and CPU processing capacity (i.e. of the microprocessor embedded in the electronic control board), and it is hence extremely inexpensive and does not require special changes of the simpler control systems for autoclaves.

However, it has been found that the measurement of the energy used up through time reading may be affected by external conditions (for example voltage drops), unrelated with the actual load size housed in the sterilisation chamber, and can hence be inaccurate.

Another indirect measurement can be that of the consumption of vaporised water. Also this approach is satisfactory, but not free from inaccuracies. As a matter of fact, in modern-concept autoclaves part of the vaporised water is generally recovered and recirculated: since the amount of recovered water can be determined only with difficulty, it is hard to establish the exact ratio between the water injected in the generator and the water actually used.

According to a preferred embodiment, hence, the energy used in the first step of the cycle is determined by integrating with the time the instant power absorbed by the autoclave components involved in the process, such power being read for example between the mains socket and the electric loads.

Alternatively, having available detection sensors on the various components which determine energy consumption in the first sterilisation step, it is possible to calculate the reading of used up energy only on such devices. For example, it can be advantageous to detect the energy used up by the steam generator and by the electric resistance for chamber heating.

Moreover, it is preferably provided to detect also the condition of a series of other devices, for example of the condensation system, to ascertain that the process cannot be affected by other factors unrelated to the load to be sterilised, such as chamber leaks, heat losses into the environment or malfunctioning of some components.

For example, during the reading step of the used energy, also the condenser temperature is continuously monitored (through a temperature sensor functionally connected to the control board), in order to determine if the temperature trend matches the value expected based on the trends of the fractionated-vacuum cycles: as a matter of fact, a possible deviation can indicate that the cooling fan is broken and hence the reading of the used up energy is distorted.

Or, during the reading step of the used up energy, from the calculation the estimate or the measurement of the energy dissipated into the environment is deducted.

It is evident that, based on the signals received from these control devices and sensors, the system can decide whether the determination of used up energy is nevertheless accurate or not. Typically, for sake of safety, if a fault of a component is detected, the system establishes that the determination of energy used up in the first step is inaccurate and hence it does not apply the reduction of drying-up times of the shortened cycle, but re-establishes the drying-up times expected for the maximum load condition.

The system of the invention, in the ways set forth above, thereby determines the energy used up in the first step of the sterilisation cycle and, after having performed the various checks on the accuracy of this reading, provides to compare it against one or more reference threshold values.

If the used up energy lies below a certain threshold value, in substance it means that the load is below a certain corresponding size. Therefore the system obtains consent to switch the control logic and to perform a short-profile sterilisation cycle, wherein the drying-up step is correspondingly shorter.

For example, with the autoclave LISA® manufactured by W&H Sterilization having a 17-lt chamber, a nominal power of 2100 W, the drying-up step for a 500-g load occurs in about 4 minutes, while with maximum load it has a duration of 16 minutes.

Therefore, in a simplified form, the control system of the invention can simply act so as to provide a 4-minute drying-up cycle, as long as a preset power absorption threshold (typically calculated in correspondence of a 500-g metal load or 200-g porous load) is not exceeded: when the summed/used energy lies above such preset threshold, the drying-up time is extended to 16 minutes.

FIG. 3 shows a "short" (phantom line) profile compared with a "standard" (full line) profile, wherefrom it can be appreciated that the first step is naturally shortened for both profiles due to the reduced load, the second exposure step is identical and the third drying-up step is set shorter by the control system of the invention.

In operation, it is provided that the system can automatically switch into performing a shortened cycle, after having determined that energy consumption is compatible with a reduced load, or that the system switches only if previously enabled to perform this function by a user. In this last case, an enabling button is provided which, if voluntarily pushed by the user, enables the apparatus to operate also with a shortened cycle; therefore the shortened cycle is performed only if two requirements are simultaneously met: one, that the determination of the energy consumption be compatible with a reduced load and hence with a reduced drying cycle and, the other, that the user has enabled the apparatus to operate with this additional functionality.

The system can preferably be configured so that it immediately sets a standard profile in normal conditions and a "short" profile whenever the user pushes the relevant button, because he believes he has a reduced load.

In this case, should the user have pressed the button of the "short" profile, the system starts already preset to run such profile. Should it be detected, during the first step of the profile, that the used up energy is compatible with a reduced load, the "short" cycle continues; in the contrary, the system switches the drying profile into "standard" and the cycle continues with the standard parameters, giving suitable warnings to the user (i.e. with a drying-up step provided for maximum load).

According to another embodiment, the system runs a further check in the final step of the drying-up cycle, at least to check that the signal coming from suitable sensors arranged in the sterilisation chamber is consistent with full load drying. In particular, since at the end of the drying step any trace of dampness should have been removed from the sterilisation chamber, heat transmission from the chamber walls cannot occur by conduction, but only by radiance. There derives that the temperature sensor arranged in the chamber is heated only by radiation, which determines a very different temperature detection. By choosing a suitably sensitive temperature sensor, it is hence possible to have proof that the drying up step has actually finished, based on the sudden temperature change detected.

Therefore, the signal coming from the temperature sensor of the chamber can be effectively used by the control logic as a further confirmation that the cycle has correctly come to the end and hence that the "short" profile is suited to load validation according to the regulations.

A further way of checking for actual load nature, can be by monitoring pressure development precisely in this last drying step.

As a matter of fact (see FIG. 4), during the drying-up step:
at fixed time intervals ($t, 2t, 3t \ldots$), the vacuum value reached upon each vacuum cycle increases proportionally to the decrease of load dampness;
at fixed pressure values ($p, p, p \ldots$) the time taken to reach the same pressure level decreases proportionally to the decrease of load dampness;
in conditions of a single, prolonged vacuum step, a change of the ratio between the pressure/time parameters is detected, which is proportional to the load dampness level.

Based on these considerations, it is possible to establish if the dampness level inside the chamber has actually reached the desired minimum values, before completing the drying-up step.

In order to optimise autoclave performance and further meet users' requirements, according to a preferred embodiment of the invention, the control system has a plurality of reference thresholds, in correspondence of an equal number of indicative loads.

By so doing, a series of incremental steps is established, based whereon the control system adapts more efficiently to the specific load within the autoclave.

For example, in the system according to the invention the following intermediate-step logic may be implemented:

| metal load | drying step time |
|---|---|
| 500 g | 5 min |
| 1000 g | 8 min |
| 2000 g | 11 min |
| 3000 g | 14 min |

Of course, the determination of the load size is carried out according to the teaching of the invention supplied here, i.e. by reading, through a suitable reading device, the amount of absorbed energy up to a well-defined point of a step preceding the start of the drying step of the sterilisation cycle, preferably the energy used/summed by one or more of the device components.

For the purposes of this application, the integral reading of the absorbed energy must not necessarily occur in exact and standardised terms (i.e., it is not necessary to have the exact value in Watt or Joule of the absorbed energy), but it is sufficient to detect a parameter which is nevertheless proportional to such consumption.

The correspondence between this quantity—whose reading can occur in the most convenient and effective position and cycle time also in the light of the specific autoclave being assessed (for example as a generic current reading over time at the input of one or more device components, for example the steam generator)—and the load which affect it, can occur experimentally. On this experimental basis, it is hence possible to determine a correspondence between energy consumption (E) and the corresponding load to be sterilised.

Thereby, a plurality of thresholds (for example $E1$-$E4 \ldots En$) are defined, in correspondence of the sample loads of reference, which determine the switching from one cycle duration to another ($t_1$-$t_4 \ldots t_n$) or in the system control logic, in order to achieve the desired optimisation according to the load. An exemplifying table might look like this:

TABLE 1

| Absorbed Energy Quantity (E) | Metal Load | Drying Step Time (t) |
|---|---|---|
| $E \leq E1$ | up to 500 g | 5 min |
| $E1 < E \leq E2$ | up to 1000 g | 8 min |
| $E1 < E \leq E3$ | up to 2000 g | 11 min |
| $E1 < E \leq E4$ | up to 3000 g | 14 min |
| $E > E4$ | over 3000 g | 16 min |

According to a system variant, alternatively to the discrete step mode, a continuous step mode is provided, possibly to be activated by the user by digiting a security password.

In the continuous mode, the drying time is proportional to the detected, absorbed energy E. The value of the drying time is obtained, in correspondence of a division into significant steps (for example obtained experimentally), as exemplifyingly shown in Table 1, further dividing the drying time evenly (for example in 1-sec steps) within each discrete cycle.

For example, taking as reference table 1, the 3-minute range existing between the two 500-g and 1000-g thresholds (which correspond experimentally to consumption values E1 and E2, respectively) is proportionally divided into further 180, 1-sec even intervals, to which the same number of values of absorbed energy is made to correspond, which energy intervals being obtained by evenly dividing the E1-E2 range. Therefore, with a drain/consumption of energy E comprised between the 500-g (E1) and 1000-g (E2) thresholds, a drying time is obtained comprised between 5'1" and 7'59".

According to a further variant, the driving logic of the system, intended to shorten the final drying step based on the overcoming of a series of different energy input thresholds, is similarly applied to some or all of the sterilisation cycles available for an autoclave.

For example, next to each of the "standard 134", "prion 134" cycles, etc. implemented as a base, the system of the invention provides corresponding "eco" modes, with a drying step reduced by discrete or continuous steps.

As can be evinced from the above-detailed description, the system of the invention fully achieves the objects set forth in the preliminary remarks.

As a matter of fact, through the determination of the energy used up in the first portion of the sterilisation cycle, the system establishes whether the load is compatible with the execution of a shortened cycle and hence provides a simple consent or a series of reliable thresholds of consent for the execution of a cycle which nevertheless meets sterilisation standards and regulations.

By reducing the duration of the cycle in the presence of reduced loads, advantageous energy and time savings are obtained, despite guaranteeing a reliable sterilisation which complies with standards and regulations.

However, it is intended that the invention is not limited to the particular embodiments illustrated above, which represent only non-limiting examples of the scope of the invention, but that a number of variants are possible, all within the reach of a person skilled in the field, without departing from the scope of the invention.

In particular, further improvements can be made to the basic system described above, without departing from the scope of protection as defined by the accompanying claims. For example,

- the energy used up can result from various parameters typical of the autoclave;
- compensation techniques depending on the temperatures can be provided, which would allow to increase calculation accuracy of the used up energy E and hence of the estimate of the load to be sterilised;
- suitable "test" cycles implemented by the logic of the control system may allow to adjust the thresholds of the various "eco" cycles to the specific sterilising apparatus; as well, it may be envisaged to develop efficiency coefficients typical of the individual autoclaves, which allow to introduce corrections so as to improve calculation accuracy in different conditions of use.

The invention claimed is:

1. A control system of a surgery autoclave capable of establishing a sterilisation cycle which comprises at least a first step of evacuation of a sterilisation chamber and of heating of a load and a final drying-up step, comprising:
   a detection device capable of detecting a parameter proportional to the energy used up at a time preceding the drying-up step, said system establishing at least a reduction of said drying-up step upon determining that said parameter of used up energy lies below a preset threshold,
   wherein said drying-up step has a first duration T, upon said determination being negative, and
   wherein said drying step has a second duration t, where t<T, upon said determination being positive, shortening the sterilisation profile.

2. The system as claimed in claim 1, further comprises a plurality of preset thresholds (E1-E4) of said parameter whereto a respective plurality of durations of said drying-up step corresponds.

3. The control system as claimed in claim 2, wherein to said preset thresholds of the used up energy parameter (E1-E4) an equal number of predetermined times of the drying-up step corresponds.

4. The system as claimed in claim 3, wherein the range between said predetermined times of the drying-up time is divided into a plurality of continuous, even steps which are associated with an equal number of values of said used up energy parameter obtained by evenly dividing the range between said preset thresholds.

5. The system as claimed in claim 4, wherein said preset thresholds of the used up energy parameter (E1-E4) are experimentally obtained, based on the required drying-up time in correspondence of preset load amounts to be sterilised, while said further continuous division is calculated.

6. The control system as claimed in claim 1, wherein said detection device is capable of performing a direct reading of the energy used.

7. The control system as claimed in claim 6, wherein said detection device is capable of performing a reading of the instant electric power used up by said autoclave and said detection is performed using the integration over time of said reading.

8. The control system as claimed in claim 6, wherein said detection device is capable of performing a reading of the instant electric power used up by one or more of a steam generator, a heater of the sterilisation chamber, a vacuum pump and a cooling fan of a condenser, belonging to the autoclave.

9. The control system as claimed in claim 1, wherein said detection device is capable of performing an indirect reading of the energy used.

10. The control system as claimed in claim 9, wherein said detection device is capable of measuring the duration over time of said first step of the sterilisation cycle.

11. The control system as claimed in claim 9, wherein said detection device is capable of measuring the amount of vaporised water in the sterilisation chamber during said first step of the sterilisation cycle.

12. The control system as in claim 1, wherein detection means of the correct functionality of the devices of the autoclave are further provided, which devices determining said used up energy in the first step of the cycle, the establishment of the reduction of the drying-up step also depending on the signals coming from said detection means of the correct functionality.

13. A surgery autoclave for the sterilisation of medical tools and products, comprising a control system as in claim 1.

14. A control system of a surgery autoclave, comprising processing means and memory means wherein a "standard" sterilisation profile is implemented, which establishes at least a first evacuation step of a sterilisation chamber and load heating and a final drying step, wherein in said processing and memory means a "short" profile or a plurality of "short" sterilisation profiles is further implemented, wherein said drying step is reduced, said "short" sterilisation profiles being set in the system in case that, through a detection device of the used up energy, it is determined that a corresponding preset threshold of energy used in said first step of the cycle is not exceeded,
   wherein said drying step has a first duration T, upon determination being negative, and
   wherein said drying step has a second duration t, where t<T, upon determination being positive, shortening the sterilisation profile.

15. A control method of a sterilisation cycle in a surgery autoclave, wherein at least a first heating and evacuation step of a sterilisation chamber and a final drying step are carried out, further comprising the steps of:
   a. detecting a parameter proportional to the energy used in a step preceding said drying cycle,
   b. determining upon said energy used being below at least a preset threshold indicative of a reduced sterilisation load,
   c. carrying out a standard sterilisation profile, wherein said drying step has a first duration T, upon said determination in step b. being negative,
   d. allowing the execution of a "short" sterilisation profile, wherein said drying step has a second duration t, where t<T, upon said determination in step b. being positive.

16. The method as claimed in claim 15, wherein, prior to said step d. there are carried out also the steps of
   e. detecting the functionality of the devices which determine said power consumption in the first step of the cycle,
   f. allowing the execution of step d. only upon in step e. it is not determined that the functionality of said devices is affected that said determination of the parameter proportional to the energy consumed being unreliable.

17. The method as claimed in claim 15, wherein a plurality of preset thresholds (E1-E4 . . . En) of said parameter of used energy are provided whereto a respective plurality of durations of said drying step ($t_1$-$t_4$ . . . $t_n$) correspond.

* * * * *